United States Patent [19]

Stähler et al.

[11] 4,002,743
[45] Jan. 11, 1977

[54] MONO- AND DITHIOPHOSPHONIC ACID ESTERS AND THEIR USE AS PESTICIDES

[75] Inventors: Gerhard Stähler, Frankfurt am Main; Ludwig Emmel, Bergen-Enkheim; Werner Bonin, Kelkheim, Taunus, all of Germany

[73] Assignee: Hoechst Aktiengesellschaft, Frankfurt am Main, Germany

[22] Filed: Mar. 18, 1975

[21] Appl. No.: 559,643

[30] Foreign Application Priority Data

Mar. 18, 1974 Germany ............... 2413008

[52] U.S. Cl. .................. 424/200; 260/307 D
[51] Int. Cl.[2] ...................... C07D 263/56
[58] Field of Search ............. 260/307 D; 424/200

[56] References Cited

UNITED STATES PATENTS

| | | | |
|---|---|---|---|
| 2,877,155 | 3/1959 | Metivier | 167/33 |
| 3,313,814 | 4/1967 | Thompson et al. | 260/251 |
| 3,657,247 | 4/1972 | Freeman et al. | 260/256.5 R |
| 3,674,803 | 7/1972 | Scherer et al. | 260/307 D |

Primary Examiner—Richard J. Gallagher
Attorney, Agent, or Firm—Curtis, Morris & Safford

[57] ABSTRACT

Mono- and dithiosphosphonic acid esters of the formula

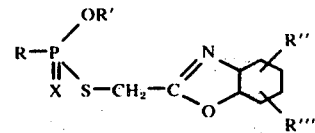

in which R is optionally substituted alkyl, cycloalkyl, cycloalkenyl, or optionally substituted phenyl, R' is optionally substituted alkyl, alkenyl, or cycloalkyl, R'' and R''' which are identical or different, are hydrogen, halogen, methyl, methoxy, nitro or trifluoromethyl, and X is oxygen or sulfur, are useful insecticides and acaricides.

16 Claims, No Drawings

MONO- AND DITHIOPHOSPHONIC ACID ESTERS AND THEIR USE AS PESTICIDES

The present invention provides mono- and dithiophosphonic acid esters of the formula I

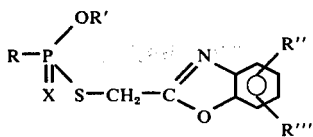

where
- R is $(C_1 - C_4)$ alkyl optionally substituted by halogen, cyano, $(C_1 - C_4)$ alkoxy, $(C_1 - C_4)$ alkylmercapto or phenyl, $(C_5 - C_6)$ cycloalkyl, $(C_5 - C_6)$ cycloalkenyl, phenyl, halophenyl, methylphenyl or methoxyphenyl,
- R' is $(C_1 - C_{12})$ alkyl, optionally substituted by halogen, cyano, $(C_1 - C_4)$ alkoxy, $(C_1 - C_4)$ alkylmercapto or phenyl, $(C_3 - C_5)$ alkenyl or $(C_5 - C_6)$ cycloalkyl,
- R'' and R''', which are identical or different, are hydrogen, halogen, methyl, methoxy, nitro or trifluoromethyl, and
- X is oxygen or sulfur.

The present invention provides furthermore a process for the preparation of compounds of formula I, which comprises reacting compounds of the formula II

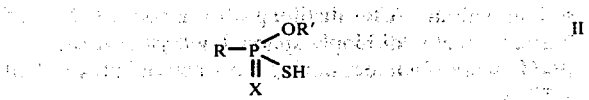

in the presence of an acid-binding agent, or salts of the compounds of formula II, with 2-halo-methylbenzoxazoles of the formula III

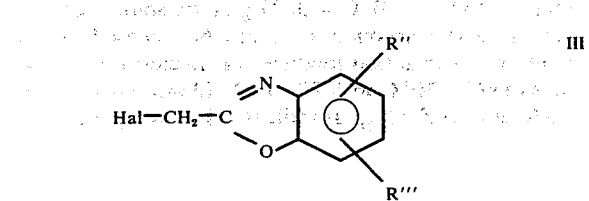

where Hal is halogen, preferably chlorine or bromine.

As acid-binding agents there may be used alkali metal hydroxides, alcoholates or carbonates, ammonia or primary, secondary or tertiary aliphatic or mixed aliphatic/aromatic amines, for example ethylamine, dimethylamine, triethylamine, dimethylaniline, or heterocyclic bases such as pyridine or quinoline. As salts of compounds of formula II, alkali metal salts, alkaline earth metal salts, ammonium salts or salts of organic bases are preferred.

The compounds of formula II or their salts are generally used in an excess of up to 10%.

The reaction is generally carried out at temperatures of from room temperature to the decomposition temperature of the final products, that is, at temperatures of from 20° to 100° C, preferably from 30° to 80° C. The reaction in exothermic in most cases and may be carried out without a solvent. However, in order to ensure a better temperature control, the reaction is advantageously carried out in inert solvents. Besides the reaction products themselves, lower aliphatic alcohols having from 1 to 4 carbon atoms, lower aliphatic ketones such as acetone or methylethylketone, short-chain aliphatic nitriles, ethers such as tetrahydrofuran or glycoldimethyl ether, amides of lower aliphatic carboxylic acids such as dimethyl formamide or dimethyl acetamide, or also water in the case of water-soluble starting materials are useful as solvents. In some cases, aromatic or chlorinated aliphatic hydrocarbons may also be used with or without addition of small amounts of the above solvents.

The compounds of the formula II and the salts thereof may be prepared in known manner, in the case of dithiophosphonic acids by reaction of the dithiophosphonic anhydrides with corresponding hydroxyl compounds, or by reaction of thionophosphoric ester chlorides with alkali metal hydrosulfides; in the case of the salts of the monothiophosphonic acids by reaction of phosphonous acid monoalkyl esters with sulfur and ammonia or by reaction of thionophosphonic acid dialkyl esters with alkali metal alcoholates.

The 2-halo-methylbenzoxazoles may be prepared according to German Pat. No. 1,300,946 by cyclization of 2-chloroacetaminophenols and elimination of water.

The compounds of the invention are insecticides and acaricides which become active on contact or on digestion. They have also systemic properties in plants and are absorbed both by the above-ground parts and roots.

Because of their properties, they are suitable for combating numerous pests of various crop plants while being well tolerated by the plants.

Numerous biting and sucking insects noxious to crop plants can be destroyed by the compounds of the invention, for example larvae of the codling moth (Carcocapsa pomonella), the diamond-back moth (Plutella maculipennis), the green oak-leaf roller (Tortrix viridana), the Asiatic cotton moth (Prodenia litura), the corn borer (Ostrinia nubilalis); aphids, such as the bean aphid (Doralis fabae), the green peach aphid (Myzodes persicae), the wooly aphid (Eriosoma lanigerum); beetle species such as the strawberry blossom weevil (Anthonomus rubi), the Mexican bean beetle (Epilachna varivestis), the Colorado beetle (Leptinotarsa decemlineata), the grain weevil (Calandra granaria), the mealworm (Tenebrio molitor); rice cicadae (Nilaparvata lugens and Nephotettix bipunctata); bugs sucking on plants such as cotton stainers (Oncopeltus fasciatus and Dysdercus fasciatus); locusts such as the North African variety of Locusta migratoria; cockroach varieties such as Periplaneta americana and Phyllodromia germanica; and spider mite varieties such as Tetranychus urticae.

The compounds of the invention are also suitable for combating ectoparasites living on productive livestock. Thus, mallophaga, lice (Anoplura), fleas (Aphaniptera), mites and ticks (Acarina, such as ixodides (Ixodidae), argasides (Argasidae), sarcoptides (Sarcoptidae), among them those resistant to phosphoric esters, are destroyed.

For the manufacture of pesticides, the compounds of formula I may be formulated in the usual admixtures with solid or liquid inert carrier substances, adhesives, wetting and dispersing agents, or grinding auxiliaries, as wettable powders, emulsion concentrates, suspensions, dusts or granules.

As carrier material, mineral substances may be used, such as aluminum silicates, argillaceous earths, kaolin, chalks, siliceous chalks, talcum, kieselguhr or hydrated silicic acids, or preparations of these mineral substances with special additives, for example chalk with sodium stearate. As a carrier material for liquid preparations, all usual and suitable organic solvents may be employed, for example toluene, xylene, dimethyl formamide, diacetone alcohol, isophorone, gasolines, paraffin oils, dioxan, dimethyl sulfoxide, ethyl acetate, butyl acetate, tetrahydrofuran, chlorobenzene and the like.

As adhesives, there may be used glue-like cellulose products or polyvinyl alcohols.

As wetting agents, all suitable emulsifiers may be used, such as oxethylated alkylphenols, salts of aryl- or alkylarylsulfonic acids, salts of ethoxylated benzenesulfonic acids, or soaps.

Suitable dispersing agents are cellulose pitch (salts of ligninsulfonic acids), salts of naphthalenesulfonic acid or, in certain cases, hydrated silicic acids or also kieselguhr.

As grinding auxiliaries, suitable inorganic or organic salts, such as sodium sulfate, ammonium sulfate, sodium carbonate, sodium bicarbonate, sodium thiosulfate, sodium stearate, sodium acetate may be used.

The pesticides may optionally be mixed with other insecticidical, nematocidal and/or fungicidal agents. These pesticides contain generally from 1 to 95% of compounds of the formula I.

The following Examples illustrate the invention.

Examples of Preparation

EXAMPLE 1:

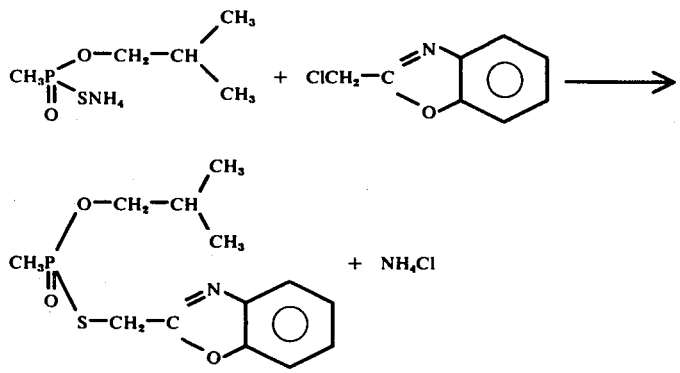

18 g of ammonium salt of methanethiolo-phosphonic acid isobutyl ester and 16 g of 2-chloromethylbenzoxazole in 100 ml of acetonitrile were heated, while stirring, for 10 minutes to 70° to 80° C. After cooling to room temperature the ammonium chloride formed was suction-filtered and the mixture was treated with 20 ml of acetonitrile. After distilling off the acetonitrile under reduced pressure, 26 g of 2-methane-o-isobutylthiolophosphonylmethyl-benzoxazole (96% of the theoretical yield) were obtained, having a refractive index $n_D^{20}$ of 1.5464.

EXAMPLE 2:

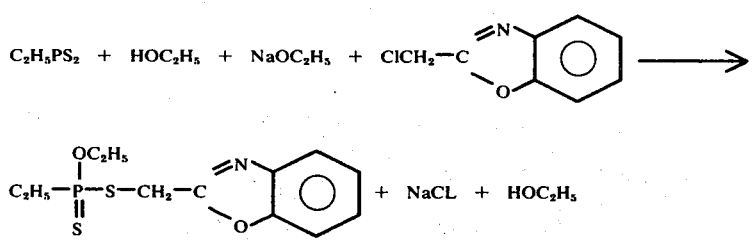

13 g of ethanedithiophosphonic anhydride were dissolved in 50 ml of ethanol, and a solution of 2.3 g of sodium in 50 ml of ethanol was added. After further addition of 16 g of 2-chloromethylbenzoxazole, the reaction mixture was heated for 10 minutes to 70° – 80° C. Subsequently, the ethanol was distilled off under reduced pressure in a rotation evaporator and the residue was diluted with 200 ml of methylene chloride. After separation by stirring with 100 ml of dilute soda solution, the organic phase was dried by means of 5 g of sodium sulfate. After distilling off the solvent, 28 g of 2-ethane-o-ethyldithiophosphonylmethylbenzoxazole (94%) were obtained, having a refractive index $n_D^{20}$ of 1.5968.

EXAMPLE 3:

69 g of propanedithiophosphonic anhydride were dissolved in 200 ml of methanol and heated for 15 minutes to 50° – 70° C with 27 g of dry sodium carbonate, until the production of gas had ceased. Subsequently, the reaction mixture was heated for 15 minutes to 60° – 70° C with 87 g of 2-chloromethylbenzoxazole and worked up as indicated in Example 2.

140 g of 2-propane-o-methyldithiophosphonylmethyl-benzoxazole were obtained having a refractive index $n_D^{20}$ of 1.600.

EXAMPLE 4:

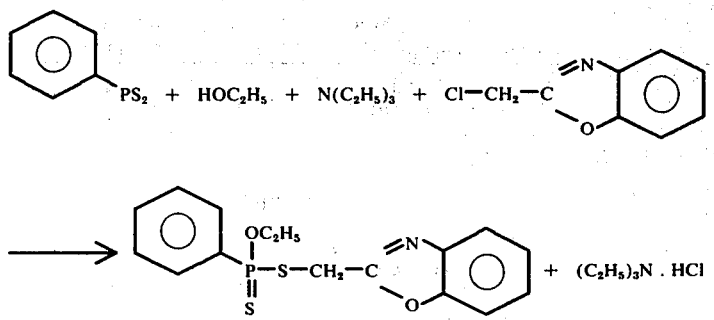

17 g of benzenedithiophosphonic anhydride in 150 ml of toluene were heated with 10 ml of ethanol to 70° – 80° C, until a homogeneous solution was obtained. To this solution, first 10 g of triethylamine and then 16 g of 2-chloromethylbenzoxazole were added with agitation. The reaction mixture was heated to 70° – 80° C for 2 hours and, after cooling to room temperature, treated twice with 100 ml each of 5% soda solution. After precipitation and drying of the organic phase with sodium sulfate, the toluene was distilled off under reduced pressure. 27 g of 2-phenyl-o-ethyldithiophosphonylmethyl-benzoxazole were obtained in the form of a slightly yellow oil, having a refractive index $n_D^{20}$ of 1.6325.

Further compounds of the formula I

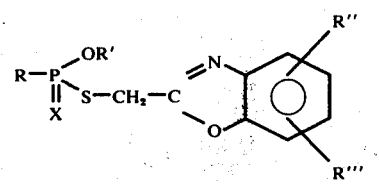

prepared according to the above 4 examples are listed in the following Table.

Table

| Example No. | compound mw | yield | physic. data | calc. | analysis % found |
|---|---|---|---|---|---|
| 5 | CH₃—P(OC₂H₅)(=S)—S—CH₂—C(benzoxazole)  287 | 93 | $n_D^{20}$ = 1.6051 | 4.9  22.3 | N  4.9  S  22.0 |
| 6 | CH₃—P(OC₂H₄OCH₃)(=S)—S—CH₂—C(benzoxazole)  317 | 94 | $n_D^{20}$ = 1.5973 | 4.4  9.8 | N  4.5  P  9.8 |
| 7 | CH₃—P(OCH₂CH=CH₂)(=S)—S—CH₂—C(benzoxazole)  299 | 96 | $n_D^{20}$ = 1.6082 | 4.6  10.4 | N  4.6  P  10.7 |
| 8 | C₂H₅—P(OCH₃)(=S)—S—CH₂—C(benzoxazole)  287 | 95 | $n_D^{20}$ = 1.6074 | 4.9  10.8 | N  5.2  P  10.9 |
| 9 | C₂H₅—P(O-n-C₃H₇)(=S)—S—CH₂—C(benzoxazole)  315 | 97 | $n_D^{20}$ = 1.5868 | 49.5  5.7  9.8 | C  49.1  H  6.0  P  10.0 |

Table-continued

| Example No. | compound / mw | yield | physic. data | calc. | analysis % | found |
|---|---|---|---|---|---|---|
| 10 | n-C₃H₇–P(=S)(OC₂H₅)–S–CH₂–C(=N–[2-methoxyphenyl]) <br> 315 | 97 | $n_D^{20}$ = 1.5842 | 4.5 <br> 9.8 | N <br> P | 4.8 <br> 9.9 |
| 11 | n-C₃H₇–P(=S)(O–n-C₃H₇)–S–CH₂–C(=N–[2-methoxyphenyl]) <br> 329 | 96 | $n_D^{20}$ = 1.5810 | 4.3 <br> 9.4 | N <br> P | 4.6 <br> 9.2 |
| 12 | n-C₃H₇–P(=S)(O–iso-C₃H₇)–S–CH₂–C(=N–[2-methoxyphenyl]) <br> 329 | 85 | $n_D^{20}$ = 1.5817 | 4.2 <br> 9.4 | N <br> P | 4.4 <br> 9.1 |
| 13 | n-C₃H₇–P(=S)(OCH₂CH=CH₂)–S–CH₂–C(=N–[2-methoxyphenyl]) <br> 327 | 85 | $n_D^{20}$ = 1.5944 | 4.2 <br> 9.5 | N <br> P | 4.4 <br> 9.5 |
| 14 | n-C₃H₇–P(=S)(O–n-C₄H₉)–S–CH₂–C(=N–[2-methoxyphenyl]) <br> 343 | 92 | $n_D^{20}$ = 1.5749 | 4.1 <br> 9.1 | N <br> P | 4.0 <br> 9.0 |
| 15 | n-C₃H₇–P(=S)(O–iso-C₄H₉)–S–CH₂–C(=N–[2-methoxyphenyl]) <br> 343 | 86 | $n_D^{20}$ = 1.5748 | 4.1 <br> 9.0 | N <br> P | 4.1 <br> 8.7 |
| 16 | n-C₃H₇–P(=S)(O–CH₂–C₆H₅)–S–CH₂–C(=N–[2-methoxyphenyl]) <br> 377 | 88 | $n_D^{20}$ = 1.6144 | 3.7 <br> 8.2 | N <br> P | 3.7 <br> 7.9 |
| 17 | n-C₄H₉–P(=S)(OC₂H₅)–S–CH₂–C(=N–[2-methoxyphenyl]) <br> 315 | 91 | $n_D^{20}$ = 1.5822 | 4.3 <br> 9.4 | N <br> P | 4.4 <br> 9.4 |
| 18 | iso-C₄H₉–P(=S)(OCH₃)–S–CH₂–C(=N–[2-methoxyphenyl]) <br> 315 | 92 | $n_D^{20}$ = 1.5906 | 4.4 <br> 9.8 | N <br> P | 4.2 <br> 9.8 |

Table-continued

| Example No. | compound mw | yield | physic. data | calc. | analysis % | found |
|---|---|---|---|---|---|---|
| 19 | iso-C₄H₉–P(=S)(O-C₂H₅)–S–CH₂–C(=N-[2-methoxyphenyl]) 329 | 85 | $n_D^{20}$ = 1.5808 | 4.3 9.4 | N P | 4.2 9.3 |
| 20 | CH₃–P(=S)(OC₂H₅)–S–CH₂–C(=N-[2-methoxy-3-chlorophenyl]) 321,5 | 98 | $n_D^{20}$ = 1.6032 | 4.4 9.6 | N P | 4.6 9.3 |
| 21 | C₂H₅–P(=S)(OC₂H₅)–S–CH₂–C(=N-[2-methoxy-3-chlorophenyl]) 335,5 | 98 | $n_D^{20}$ = 1.6010 | 4.2 9.2 | N P | 4.5 9.2 |
| 22 | n-C₃H₇–P(=S)(OC₂H₅)–S–CH₂–C(=N-[2-methoxy-3-chlorophenyl]) 349,5 | 97 | $n_D^{20}$ = 1.5929 | 4.0 8.9 | N P | 3.9 8.7 |
| 23 | C₆H₅–P(=S)(OC₂H₅)–S–CH₂–C(=N-[2-methoxy-3-chlorophenyl]) 383,5 | 94 | $n_D^{20}$ = 1.6388 | 3.9 8.0 | N P | 3.9 8.1 |
| 24 | CH₃–P(=S)(OC₂H₅)–S–CH₂–C(=N-[4-chloro-2-methoxyphenyl]) 321,5 | 90 | $n_D^{20}$ = 1.6112 | 11.1 9.6 | Cl P | 10.7 9.7 |
| 25 | C₂H₅–P(=S)(OC₂H₅)–S–CH₂–C(=N-[4-chloro-2-methoxyphenyl]) 335,5 | 98 | $n_D^{20}$ = 1.6020 | 10.6 9.2 | Cl P | 10.4 9.1 |
| 26 | n-C₃H₇–P(=S)(OC₂H₅)–S–CH₂–C(=N-[4-chloro-2-methoxyphenyl]) 349,5 | 92 | $n_D^{20}$ = 1.5948 | 10.2 8.8 | Cl P | 10.0 8.7 |
| 27 | iso-C₄H₉–P(=S)(OC₂H₅)–S–CH₂–C(=N-[4-chloro-2-methoxyphenyl]) 363,5 | 94 | $n_D^{20}$ = 1.5861 | 9.5 8.5 | Cl P | 9.2 8.2 |
| 28 | CH₃–P(=S)(OC₂H₅)–S–CH₂–C(=N-[5-chloro-2-methoxyphenyl]) 321,5 | 87 | $n_D^{20}$ = 1.6207 | 4.4 9.6 | N P | 4.8 9.1 |

Table-continued

| Example No. | compound / mw | yield | physic. data | calc. | analysis % found |
|---|---|---|---|---|---|
| 29 | [C₂H₅-P(OC₂H₅)(=S)-S-CH₂-C(=N-)... 2-OCH₃, 4-Cl phenyl]  335,5 | 93 | $n_D^{20}$= 1.6131 | 10.6 9.2 | Cl 11.0 P 8.9 |
| 30 | [n-C₃H₇-P(OC₂H₅)(=S)-S-CH₂-C(=N-)... 2-OCH₃, 4-Cl phenyl]  349,5 | 92 | $n_D^{20}$= 1.6022 | 10.2 8.9 | Cl 10.9 P 8.6 |
| 31 | [iso-C₄H₉-P(OC₂H₅)(=S)-S-CH₂-C(=N-)... 2-OCH₃, 4-Cl phenyl]  363,5 | 91 | $n_D^{20}$= 1.5930 | | |
| 32 | [phenyl-P(OC₂H₅)(=S)-S-CH₂-C(=N-)... 2-OCH₃, 4-Cl phenyl] | 86 | $n_D^{20}$= 1.6442 | 9.3 8.1 | Cl 9.8 P 7.8 |
| 33 | [CH₃-P(OC₂H₅)(=S)-S-CH₂-C(=N-)... 2-OCH₃, 4,6-diCl phenyl]  356 | 98 | m.p. 72–73° C | 20.0 18.0 | Cl 20.1 S 17.9 |
| 34 | [CH₃-P(O-iso-C₄H₉)(=S)-S-CH₂-C(=N-)... 2-OCH₃, 4,6-diCl phenyl] | 85 | $n_D^{20}$= 1.5649 | 19.2 8.3 | Cl 19.2 P 7.9 |
| 35 | [C₂H₅-P(OC₂H₅)(=S)-S-CH₂-C(=N-)... 2-OCH₃, 4,6-diCl phenyl]  370 | 84 | m.p. 38–39° C | 3.8 17.3 | N 4.0 S 17.5 |
| 36 | [n-C₄H₉-P(OC₂H₅)(=S)-S-CH₂-C(=N-)... 2-OCH₃, 4,6-diCl phenyl]  398 | 96 | m.p. 47–48° C | 17.8 16.2 | Cl 18.0 S 16.0 |
| 37 | [phenyl-P(OC₂H₅)(=S)-S-CH₂-C(=N-)... 2-OCH₃, 4,6-diCl phenyl]  418 | 95 | m.p. 43–44° C | 17.0 15.3 | Cl 17.2 S 14.9 |
| 38 | [benzyl-CH₂-P(OC₂H₅)(=S)-S-CH₂-C(=N-)... 2-OCH₃, 4,6-diCl phenyl]  432 | 93 | $n_D^{20}$= 1.6295 | 16.4 7.2 | Cl 15.9 P 7.2 |

Table-continued

| Example No. | compound mw | yield | physic. data | calc. | analysis % found | |
|---|---|---|---|---|---|---|
| 39 | (phenyl)(OC₂H₅)P(=O)-S-CH₂-C(=N-(2-OCH₃-3,5-diCl-phenyl)) 402 | 86 | $n_D^{20}$=1.5877 | 17.8 7.6 | Cl S | 18.2 7.3 |
| 40 | (C₂H₅O)(C₂H₅)P(=S)-S-CH₂-C(=N-(2-OCH₃-5-CH₃-phenyl)) 315 | 95 | $n_D^{20}$=1.5868 | 4.4 9.8 | N P | 4.9 9.5 |
| 41 | (C₂H₅O)(C₃H₇)P(=S)-S-CH₂-C(=N-(2-OCH₃-5-CH₃-phenyl)) 329 | 92 | $n_D^{20}$=1.5809 | 4.3 9.4 | N P | 4.5 9.1 |
| 42 | (C₂H₅O)(CH₃)P(=S)-S-CH₂-C(=N-(2-OCH₃-4,5-diCH₃-phenyl)) 315 | 98 | m.p. 34–35°C | 4.4 9.8 | N P | 4.2 9.7 |
| 43 | (C₂H₅O)(C₂H₅)P(=S)-S-CH₂-C(=N-(2-OCH₃-4,5-diCH₃-phenyl)) 329 | 97 | m.p. 49–50°C | 4.2 9.4 | N P | 4.2 9.2 |
| 44 | (C₂H₅O)(C₃H₇)P(=S)-S-CH₂-C(=N-(2-OCH₃-4,5-diCH₃-phenyl)) 343 | 98 | m.p. 51–52°C | 4.1 9.0 | N P | 4.4 9.1 |
| 45 | (C₂H₅O)(iso-C₄H₉)P(=S)-S-CH₂-C(=N-(2-OCH₃-4,5-diCH₃-phenyl)) 357 | 97 | $n_D^{20}$=1.5739 | 3.9 8.7 | N P | 3.6* 8.8 |
| 46 | (C₂H₅O)(phenyl)P(=S)-S-CH₂-C(=N-(2-OCH₃-4,5-diCH₃-phenyl)) 377 | 81 | m.p. 44–45°C | 3.7 8.2 | N P | 3.8 8.3 |
| 47 | (C₂H₅O)(CH₃)P(=S)-S-CH₂-C(=N-(2-OCH₃-5-NO₂-phenyl)) 332 | 95 | $n_D^{20}$=1.6188 | 8.5 9.3 | N P | 8.3 8.8 |
| 48 | (C₂H₅O)(C₃H₅)P(=S)-S-CH₂-C(=N-(2-OCH₃-5-NO₂-phenyl)) 346 | 93 | $n_D^{20}$=1.6071 | 7.8 8.9 | N P | 7.8 8.6 |

Table-continued
| Example No. | compound mw | yield | physic. data | calc. | analysis % found |
|---|---|---|---|---|---|
| 49 | 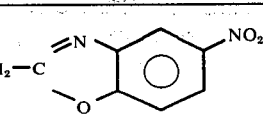 360 | 96 | m.p. 54–55°C | 7.5 8.6 | N 7.5 P 8.5 |
| 50 | 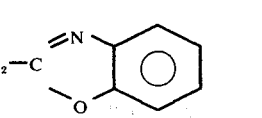 374 | 95 | m.p. 66–67°C | 7.5 8.3 | N 7.6 P 7.9 |
| 51 | 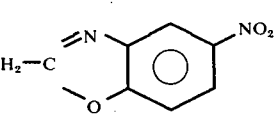 374 | 96 | m.p. 70–71°C | 7.5 8.3 | N 7.6 P 8.6 |
| 52 | 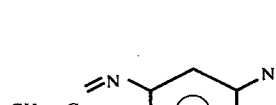 | 97 | m.p. 78–79°C | 7.1 7.8 | N 6.9 P 7.9 |
| 53 |  | 75 | m.p. 96–97°C | 6.6 7.3 | N 6.8 P 7.2 |
| 54 | 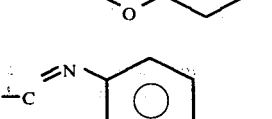 332 | 96 | m.p. 62–63°C | 8.4 9.3 | N 8.7 P 8.8 |
| 55 | 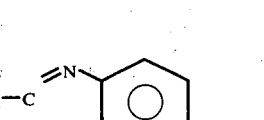 346 | 97 | m.p. 44°C | 8.1 9.0 | N 8.2 P 9.2 |
| 56 | 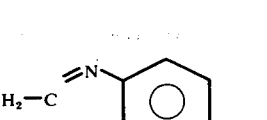 360 | 93 | m.p. 37°C | 7.8 8.6 | N 7.4 P 8.6 |
| 57 | 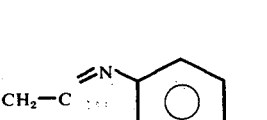 374 | 95 | m.p. 54–55°C | 7.5 8.2 | N 7.3 P 8.1 |
| 58 |  394 | 93 | m.p. 76–77°C | 7.1 7.9 | N 7.4 P 7.9 |

Table-continued

| Example No. | compound mw | yield | physic. data | calc. | analysis % | found |
|---|---|---|---|---|---|---|
| 59 | [structure: 3-methoxyphenyl-P(=S)(OC₂H₅)-S-CH₂-C(=N-Ar)- where Ar = 2-methoxy-4-nitrophenyl] 424 | 85 | m.p. 104–105°C | 6.8 7.3 | N P | 6.8 7.4 |
| 60 | [structure: benzyl-P(=S)(OC₂H₅)-S-CH₂-C(=N-Ar)-, Ar = 2-methoxy-4-nitrophenyl] | 96 | $n_D^{20}$ = 1.6414 | 6.9 7.6 | N P | 6.9 7.4 |
| 61 | [structure: cyclohexyl(H)-P(=S)(OC₂H₅)-S-CH₂-C(=N-Ar)-, Ar = 2-methoxy-4-nitrophenyl] 400 | 98 | m.p. 77–78°C | 7.0 7.7 | N P | 6.7 7.6 |
| 62 | [structure: CH₃-P(=S)(OC₂H₅)-S-CH₂-C(=N-Ar)-, Ar = 2-methoxy-6-chloro-4-nitrophenyl] 366,5 | 91 | $n_D^{20}$ = 1.6338 | 7.6 8.4 | N P | 7.6 8.2 |
| 63 | [structure: C₃H₇-P(=S)(OC₂H₅)-S-CH₂-C(=N-Ar)-, Ar = 2-methoxy-6-chloro-4-nitrophenyl] 394,5 | 93 | m.p. 47°C | 7.1 7.8 | N P | 7.0 7.7 |
| 64 | [structure: iso-C₄H₉-P(=S)(OC₂H₅)-S-CH₂-C(=N-Ar)-, Ar = 2-methoxy-6-chloro-4-nitrophenyl] 408,5 | 90 | m.p. 45°C | 6.8 7.6 | N P | 6.8 7.3 |
| 65 | [structure: phenyl-P(=S)(OC₂H₅)-S-CH₂-C(=N-Ar)-, Ar = 2-methoxy-6-chloro-4-nitrophenyl] 428,5 | 88 | m.p. 119°C | 6.6 7.3 | N P | 6.8 7.4 |
| 66 | [structure: CH₃-P(=S)(OC₂H₅)-S-CH₂-C(=N-Ar)-, Ar = 6-chloro-2-methoxy-4-nitro... variant] 366,5 | 94 | m.p. 156–158°C | 7.7 8.5 | N P | 7.6 8.6 |
| 67 | [structure: C₂H₅-P(=S)(OC₂H₅)-S-CH₂-C(=N-Ar)-, Ar = chloro-methoxy-nitrophenyl] 380,5 | 90 | m.p. 140–141°C | 7.4 8.2 | N P | 7.1 7.9 |

Table-continued

| Example No. | compound mw | yield | physic. data | calc. | analysis % | found |
|---|---|---|---|---|---|---|
| 68 | (3-OCH$_3$-C$_6$H$_4$)(OC$_2$H$_5$)P(=S)-S-CH$_2$-C(=N-2-OCH$_3$-C$_6$H$_4$)<br>mw 379 | 92 | $n_D^{20}$ = 1.6292 | 3.7<br>16.9 | N<br>S | 3.8<br>16.9 |
| 69 | (C$_6$H$_5$-CH$_2$)(OC$_2$H$_5$)P(=S)-S-CH$_2$-C(=N-2-OCH$_3$-C$_6$H$_4$)<br>mw 363 | 93 | m.p. 96–98°C | 3.8<br>8.5 | N<br>P | 3.8<br>8.3 |
| 70 | (cyclo-C$_6$H$_{11}$)(OC$_2$H$_5$)P(=S)-S-CH$_2$-C(=N-2-OCH$_3$-C$_6$H$_4$)<br>mw 355 | 94 | $n_D^{20}$ = 1.5948 | 4.0<br>18.1 | N<br>P | 4.1<br>18.0 |
| 71 | (C$_2$H$_5$)(OC$_2$H$_5$)P(=S)-S-CH$_2$-C(=N-(5-CF$_3$-2-OCH$_3$-4-Cl-C$_6$H$_2$))<br>mw 403.5 | 92 | $n_D^{20}$ = 1.5499 | 14.1<br>7.6 | F<br>P | 13.5<br>7.2 |

BIOLOGICAL EXAMPLES

EXAMPLES I

Bean plants heavily infested with spider mites (*Tetranychus urticae*) were sprayed with an aqueous dilution of an emulsion concentrate containing 0.003 weight % of the compound of Example 25 until dripoff began. Subsequently, the plants were placed in a greenhouse at 20° C. Upon microscopic control 8 days after spraying, all mobile and immobile phases of the mite population were destroyed.

Tested in the same way, the compounds according to Examples 2, 5, 8, 9, 12, 13, 15, 20, 21, 27, 28, 29, 33, 47, 48, 49, 50, 54, 56, 62, 66, 71 proved to be equally efficient.

On comparison, commercial phosphoric esters had the following effect:

| Compound | Application concentration | Killing rate |
|---|---|---|
| (C$_2$H$_5$O)$_2$P(=S)-S-CH$_2$-C(=N-)(3,5-diCl-benzoxazine)<br>Batestan | 0.006 % | 80 % |
| (C$_2$H$_5$O)$_2$P(=S)-S-CH$_2$-N(=C(=O)-O-)(5-Cl-C$_6$H$_3$)<br>Phosalone | 0.003 % | 65 % |
| (C$_2$H$_5$O)$_2$P(=S)-O-C(=N-C(CH$_3$)$_2$)(pyrimidine-CH$_3$)<br>Diazinon | 0.025 % | 70 % |

-continued

| Compound | Application concentration | Killing rate |
|---|---|---|
| (CH₃O)₂P(=O)—CH(OH)—CCl₃  Dipterex | 0.1 % | 30 % |
| 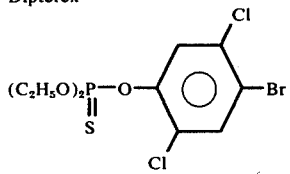  Bromophos | 0.1 % | 0 % |

EXAMPLE II

Horse beans (*Vicia faba*) heavily infested with bean aphids (*Doralis fabae*) were sprayed, until drip-off began, with the aqueous suspension of a wetting powder containing 0.000375 weight % of the compound of Example 5. The sprayed plants were then placed at 20° C in a greenhouse; evaluation was carried out 24 hours after the spraying. All aphids were killed.

Tested in the same manner, the compounds of Examples 1, 25, 26, 27, 29, 34, 37, 47, 48, 50, 56 showed equal activity.

EXAMPLE III

Young cotton plants (Gossypium spec.) in pots, infested with 40 African cotton stainers (*Dysdercus fasciatus*), were sprayed until drip-off began, with the aqueous dilution of an emulsifiable concentrate containing 0.006 weight % of the compound of Example 1. Subsequently, the plants containing the bugs were put into cylindrical gauze cages in a green-house at 22° C. A control after 48 hours showed that all cotton stainers were killed.

Tested in the same manner, the compounds of Examples 1, 2, 3, 5, 6, 9, and 47 showed the same good activity.

In contrast, for destroying *Dysdercus fasciatus* using the commercial compound of the formula

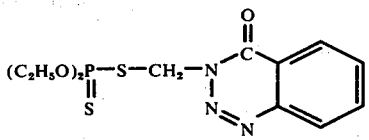

known under the trade name of azinphos-ethyl, a 0.025% concentration of active substance, was needed using bromophos, a concentration of active substance of 0.1% was needed.

EXAMPLE IV 50 larvae (4th stage) of the Mexican bean beetle (*Epilachna varivestis*) and leaves of the dwarf-bush bean (*Phaseolus vulgaris*) were sprayed, by means of a spraying apparatus, with a dosed amount (corresponding to an application amount of 600 liters of spray liquor/ha in the open fields) of the aqueous dilution of an emulsifiable concentrate containing the compound of Example 34 in a concentration of 0.0025 weight %. The leaves and beetle larvae were placed in open vessels at 22° C. The control 48 hours after spraying proved that all larvae were killed.

Tested in the same manner, the compounds of Examples 1, 2, 6, 10, 11, 17, 25, 26, 29, 30, 36, 37 and 62 showed equal activity.

By comparison, the following concentrations of commercial active substance were required to kill completely *Epilachna varivestis*:

| | |
|---|---|
| (CH₃O)₂P(=S)—S—CH₂—N—C(=O)—N(—S—)—C(OCH₃)  Methidathion | 0.01 % |
| (CH₃O)₂P(=O)—O—C(CH₃)=CClCON(C₂H₅)₂  Phosphamidon | 0.02 % |

EXAMPLE V 50 larvae (3rd stage) of the Egyptian cotton moth (*Prodenia litura*) and cotton leaves were sprayed with a defined amount (corresponding to 600 liters of spray liquor/ha) of an aqueous dilution of an emulsifiable concentrate containing the active substance of Example 34, and subsequently placed in open vessels at 22° C. Evaluation was carried out after 48 hours. A concentration of 0.005% of active substance was sufficient to kill all test animals within the cited period.

By comparison, in order to kill *Prodenia litura* completely by means of commercial active substances, the following concentrations were needed:

| | |
|---|---|
| Batestan | 0.05 % |
| Methidathion | 0.05 % |
| (CH₃O)₂P(=S)—S—CH₂C(=C)NHCH₃  Dimethoate | 0.05 % |

EXAMPLE VI

The systemic properties of the compounds of the invention were proved in the following test: Horse beans (*Vicia faba*) infested with bean aphids (*Doralis fabae*) were provided at the lower end of the stem with a cotton wool dressing wrapped in a sheet, in which dressing 0.5 mg of the active substance of Example 41 in an aqueous emulsion was uniformly spread. The sheet wrapping served to prevent the development of a gas phase. The plants were then placed in a greenhouse at 20° C. The active substance rapidly penetrated the green plant stems and moved to the upper plant parts, within a few hours killing all aphids.

The same result was obtained using the active substances of Examples 1 and 8.

EXAMPLE VII

In vitro test on tropical cattle ticks (*Boophilus microplus*)

For the preparation of a suitable formulation, 10% (G/V) of active substance was dissolved in a mixture of cyclohexanone and nonylphenol (8:1), and the emulsifiable concentrate so obtained was diluted with water of 12° of German hardness to attain the desired concentration.

10 female ticks each of *Boophilus microplus*,
a. strain Mexico, phosphoric ester sensitive
b. strain Biarra, phosphoric ester resistant which had sucked themselves full of blood, were dipped for 5 minutes into these dilutions. Subsequently, the ticks were stuck on their dorsal sides to an adhesive tape and kept in a warming closet (28° C, about 80% of relative air moisture) for oviposition.

For a control, female ticks were dipped into water.
The effect was evaluated as follows:
2 weeks after the treatment, a. inhibition of oviposition, 100% meaning that none of the ticks oviposited, 0% meaning that all ticks did oviposit (column (a) of the Table)

b. size of the egg agglomerations in % compared with the egg agglomerations of the control ticks, 100% meaning that the size was the same as that of the control ticks, 0% meaning that there were no eggs (column (b) of the table) 5 weeks after treatment c. hatching rate of the larvae, 100% meaning that larvae emerged from all eggs, 0% meaning that no larvae emerged (column (c) of the Table).

From the results of (a), (b) and (c) the total damage to the tick population (d) was calculated according to the following equation:

$$d\ (\%) = 100 - \left[ (100 - a) \cdot \frac{b}{100} \cdot \frac{c}{100} \right].$$

The results of the tests using the compounds of the invention compared with a commercial product for combating ticks are listed in the following Table:

| Formula of active substance (AS) and Example No. | AS concentration in % | Strain Mexico | | | | Strain Biarra | | | |
|---|---|---|---|---|---|---|---|---|---|
| | | a | b | c | d | a | b | c | d |
| (2) | 0.2 | 100 | 0 | 0 | 100 | 100 | 0 | 0 | 100 |
| | 0.05 | 80 | 43 | 10 | 100 | 80 | 48 | 0 | 100 |
| | 0.012 | 70 | 32 | 10 | 99 | 40 | 59 | 50 | 98 |
| | 0.003 | 70 | 42 | 10 | 98 | 20 | 56 | 100 | 95 |
| (5) | 0.2 | 100 | | 0 | 100 | 90 | 56 | 0 | 100 |
| | 0.05 | 90 | 78 | 5 | 100 | 90 | 56 | 0 | 100 |
| | 0.012 | 80 | 58 | 10 | 90 | 10 | 38 | 30 | 21 |
| | 0.003 | 80 | 58 | 10 | 90 | 10 | 65 | 50 | 38 |
| (6) | 0.2 | 100 | 0 | 0 | 100 | 100 | 0 | 0 | 100 |
| | 0.05 | 100 | 0 | 0 | 100 | 80 | 13 | 0 | 100 |
| | 0.012 | 60 | 77 | 5 | 97 | 20 | 61 | 100 | 51 |
| | 0.003 | 10 | 79 | 10 | 93 | 0 | 91 | 100 | 9 |
| (8) | 0.2 | 100 | 0 | 0 | 100 | 80 | 70 | 100 | 86 |
| | 0.05 | 100 | 0 | 0 | 100 | 70 | 88 | 100 | 38 |
| | 0.012 | 100 | 0 | 0 | 100 | 10 | 100 | 100 | 10 |
| | 0.003 | 90 | 35 | 0 | 100 | 0 | 100 | 100 | 0 |
| (10) | 0.2 | 90 | 29 | 0 | 100 | 80 | 13 | 5 | 98 |
| | 0.05 | 100 | 0 | 0 | 100 | 80 | 50 | 10 | 90 |
| | 0.012 | 90 | 10 | 0 | 100 | 0 | 45 | 100 | 55 |
| | 0.003 | 80 | 58 | 50 | 94 | 0 | 18 | 100 | 82 |
| (11) | 0.2 | 100 | 0 | 0 | 100 | 100 | 0 | 0 | 100 |
| | 0.05 | 100 | 0 | 0 | 100 | 90 | 7 | 0 | 100 |
| | 0.012 | 100 | 0 | 0 | 100 | 70 | 26 | 30 | 97 |
| | 0.003 | 60 | 43 | 0 | 100 | 10 | 69 | 60 | 59 |

-continued

| Formula of active substance (AS) and Example No. | AS concentration in % | Strain Mexico a | b | c | d | Strain Biarra a | b | c | d |
|---|---|---|---|---|---|---|---|---|---|
| (13) | 0.2 | 100 | 0 | 0 | 100 | 100 | 0 | 0 | 100 |
| | 0.05 | 100 | 0 | 0 | 100 | 60 | 30 | 20 | 97 |
| | 0.012 | 90 | 41 | 20 | 99 | 20 | 100 | 80 | 36 |
| | 0.003 | 50 | 19 | 50 | 97 | 0 | 94 | 100 | 6 |
| (20) | 0.2 | 100 | 0 | 0 | 100 | 80 | 23 | 10 | 99 |
| | 0.05 | 90 | 31 | 0 | 100 | 100 | 0 | 0 | 100 |
| | 0.012 | 80 | 36 | 0 | 100 | 70 | 40 | 20 | 97 |
| | 0.003 | 80 | 45 | 20 | 98 | 50 | 48 | 50 | 88 |
| (25) | 0.2 | 100 | 0 | 0 | 100 | 100 | 0 | 0 | 100 |
| | 0.05 | 100 | 0 | 0 | 100 | 100 | 0 | 0 | 100 |
| | 0.012 | 100 | 0 | 0 | 100 | 90 | 40 | 0 | 100 |
| | 0.003 | 90 | 21 | 30 | 99 | 10 | 58 | 100 | 48 |
| (21) | 0.2 | 100 | 0 | 0 | 100 | 100 | 0 | 0 | 100 |
| | 0.05 | 100 | 0 | 0 | 100 | 90 | 7 | 20 | 100 |
| | 0.012 | 90 | 63 | 20 | 98 | 70 | 60 | 80 | 98 |
| | 0.003 | 70 | 34 | 50 | 95 | 0 | 80 | 100 | 20 |
| (29) | 0.2 | 90 | 15 | 0 | 100 | 100 | 0 | 0 | 100 |
| | 0.05 | 80 | 27 | 20 | 99 | 70 | 12 | 20 | 99 |
| | 0.012 | 80 | 38 | 40 | 97 | 50 | 53 | 80 | 70 |
| | 0.003 | 70 | 85 | 80 | 90 | 90 | 79 | 100 | 21 |
| (47) | 0.2 | 100 | 0 | 0 | 100 | 90 | 7 | 10 | 99 |
| | 0.05 | 100 | 0 | 0 | 100 | 60 | 26 | 50 | 94 |
| | 0.012 | 90 | 9 | 0 | 100 | 60 | 96 | 50 | 72 |
| | 0.003 | 100 | 0 | 0 | 100 | 60 | 70 | 100 | 30 |
| (55) | 0.2 | 100 | 0 | 0 | 100 | 80 | 40 | 30 | 97 |
| | 0.05 | 100 | 0 | 0 | 100 | 80 | 63 | 50 | 94 |
| | 0.012 | 100 | 0 | 0 | 100 | 10 | 64 | 80 | 48 |
| | 0.003 | 80 | 22 | 10 | 99 | 10 | 80 | 100 | 30 |
| Batestan, commercial | 0.2 | 100 | 0 | 0 | 100 | 0 | 86 | 100 | 14 |
| | 0.05 | 90 | 16 | 10 | 99 | 10 | 80 | 100 | 28 |
| | 0.012 | 70 | 12 | 10 | 99 | 0 | 78 | 100 | 22 |
| | 0.003 | 30 | 73 | 100 | 49 | 0 | 78 | 100 | 22 |

What is claimed is:
1. A mono- or dithiophosphonic acid ester of the formula

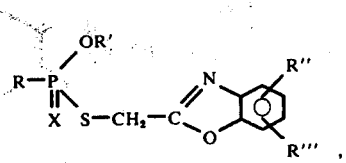

wherein
R is alkyl of from 1 to 4 carbon atoms optionally substituted by halogen, alkoxy of from 1 to 4 carbon atoms, alkylmercapto of from 1 to 4 carbon atoms or phenyl; cycloalkyl of 5 or 6 carbon atoms; phenyl; halophenyl; methylphenyl or methoxyphenyl;

R' is alkyl of from 1 to 12 carbon atoms optionally substituted by halogen, alkoxy of from 1 to 4 carbon atoms, alkylmercapto of from 1 to 4 carbon atoms or phenyl; alkenyl of from 3 to 5 carbon atoms or cycloalkyl of from 3 to 5 carbon atoms;

R" and R''', which are identical or different, are hydrogen, halogen, methyl, methoxy, nitro or trifluoromethyl; and X is oxygen or sulfur.

2. A composition for combating a parasitic insect, mite or tick, which comprises 1 to 95% by weight of a compound defined in claim 1 and a solid or liquid inert carrier substance, an adhesive, a wetting agent, a dispersing agent or a grinding auxiliary.

3. A method for combating a parasitic insect or mite infesting a crop plant or a parasitic insect, mite or tick living on a livestock animal, which comprises contacting with the surface of said crop plant, to effect deposition on said surface or absorption into said plant, or administering cutaneously to said livestock animal an effective amount of a compound defined in claim 18 introduced in a composition comprising 1 to 95% by weight of said compound and a solid or liquid inert carrier substance, an adhesive, a wetting agent, a dispersing agent or a grinding auxiliary.

4. The compound of the formula

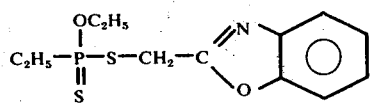

5. The compound of the formula

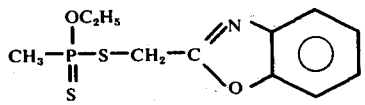

6. The compound of the formula

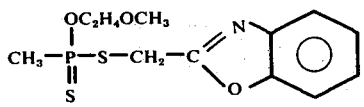

7. The compound of the formula

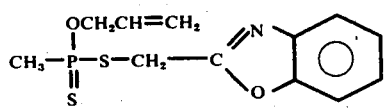

8. The compound of the formula

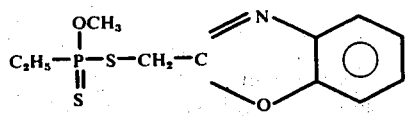

9. The compound of the formula

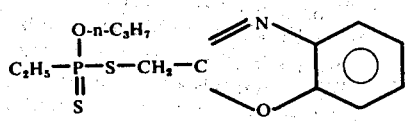

10. The compound of the formula

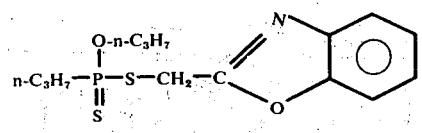

11. The compound of the formula

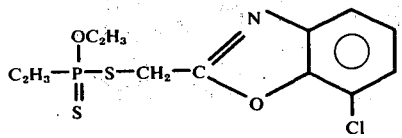

12. The compound of the formula

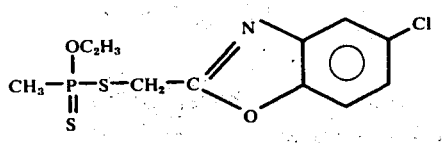

13. The compound of the formula

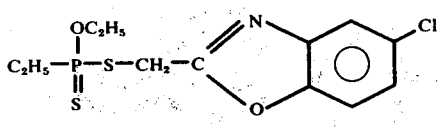

14. The compound of the formula

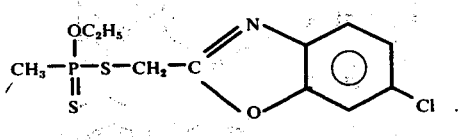

15. The compound of the formula

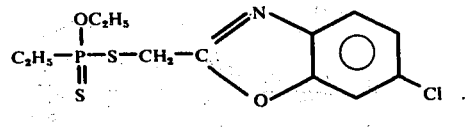

16. The compound of the formula

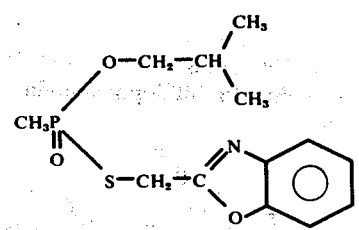

* * * * *